(12) United States Patent
Gingera et al.

(10) Patent No.: US 9,161,502 B2
(45) Date of Patent: Oct. 20, 2015

(54) BRASSICA JUNCEA LINES WITH A CANOLA FATTY ACID PROFILE

(75) Inventors: Gregory R. Gingera, Saskatoon (CA); James Brent Gillespie, Toronto (CA)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 1388 days.

(21) Appl. No.: 12/269,101

(22) Filed: Nov. 12, 2008

(65) Prior Publication Data

US 2009/0136646 A1    May 28, 2009

Related U.S. Application Data

(60) Provisional application No. 60/987,476, filed on Nov. 13, 2007.

(51) Int. Cl.
A01H 5/00 (2006.01)
A01H 5/10 (2006.01)
A01H 1/00 (2006.01)

(52) U.S. Cl.
CPC ........................................ A01H 5/10 (2013.01)

(58) Field of Classification Search
None
See application file for complete search history.

(56) References Cited

U.S. PATENT DOCUMENTS

| | | | |
|---|---|---|---|
| 6,303,849 B1 * | 10/2001 | Potts et al. | 800/306 |
| 6,414,223 B1 | 7/2002 | Kodali | |
| 6,441,278 B1 | 8/2002 | DeBonte et al. | |
| 6,737,564 B2 | 5/2004 | Yao et al. | |
| 6,787,686 B2 | 9/2004 | Potts et al. | |
| 2003/0221217 A1 | 11/2003 | Yao et al. | |
| 2008/0168587 A1 | 7/2008 | Yao et al. | |

FOREIGN PATENT DOCUMENTS

| | | |
|---|---|---|
| AU | 2004203364 A1 | 2/2006 |
| CA | 2471884 A1 | 1/2006 |

OTHER PUBLICATIONS

Burton, W.A., et al.; "Assessment of genetic diversity in selected breeding lines and cultivars of canola quality *Brassica juncea* and their implications for canola breeding"; Euphytica (Mar. 1, 2004) 136(2):181-192; Kluwer Academic Publishers, The Netherlands.
Pradhan, A.K., et al.; "A high-density linkage map in *Brassica juncea* (Indian mustard) using AFLP and RFLP Markers" Theoretical and Applied Genetics (Feb. 1, 2003) 106(4):607-614; Springer, Berlin, Germany.
BB1868AU$_{13}$ Examination$_{13}$ Report$_{13}$ No.1$_{13}$ Dated$_{13}$ Apr. 24, 2013.
BB1868CA$_{13}$ CA Office Action$_{13}$ Dated$_{13}$ Dec. 19, 2011.
BB1868CA$_{13}$ CA Office Action$_{13}$ Dated$_{13}$ Feb. 11, 2013.
BB1868CA$_{13}$ CA Office Action$_{13}$ Dated$_{13}$ Feb. 25, 2014.

* cited by examiner

*Primary Examiner* — Elizabeth McElwain

(57) ABSTRACT

*Brassica juncea* having greater than about 55% oleic acid per weight of total fatty acid and methods of producing same are provided. The new *Brassica juncea* lines produce oil having the typical canola fatty acid profile. Methods for producing progeny *Brassica juncea* plants produced by crossing the high oleic acid *Brassica juncea* line with itself or with other canola plants, and hybrid canola seeds and plants produced by crossing the *Brassica juncea* high oleic acid line with another canola line or plant, are provided.

8 Claims, 9 Drawing Sheets

Figure 9

| Spring 1999 |
| --- |
| 8 Pioneer low glucosinolate B. juncea lines mixed to form bulk population |

| Summer 1999 |
| --- |
| EMS treated population grown in Saskatoon, SK |
| 6403 open-pollinated (OP) plants harvested and analyzed for fatty acid composition |
| No OP plants identified with acceptable canola fatty acid profile - highest 52.83% oleic acid |

| Fall 1999 |
| --- |
| Created new population of top 500 oleic acid content from Summer 1999 experiment |
| Population re-mutagenized and grown in Mexico |
| 3614 OP plants harvested and analyzed for fatty acid composition |
| Several putative high oleic individuals identified - 286, 338, 1060, 1629, 2397, 4327, 4561 and 4964 |

| Spring 2000 |
| --- |
| Half-seed analysis to purify high oleic sources |
| Compared half-seed to original plant for 286 and 338 sources |
| Made F1's of high x low oleic acid |

| Summer 2000 | Summer 2000 |
| --- | --- |
| Half-seed analysis to compare stability from spring lines<br>Evaluated F2's of high x low oleic acid - made new F1's of high x low oleic acid for Round 2 | Field characterization of 338 and 1629 sources in Rosetown, SK to demonstrate field stability and characterize quality |

| Fall 2000 | Fall 2000 |
| --- | --- |
| Round 2 F1 oleic acid stability evaluated in SJ-210 | 51 lines sent to Chile for seed increase in preparation for 2001 multi-location yield and disease trials |

| Summer 2001 | Summer 2001 |
| --- | --- |
| Evaluation of Round 2 selections for increased oil content and reduced glucosinolate content | 6 locations of yield trials for agronomy and quality<br>1 location of assessment for blackleg resistance using check varities |

BRASSICA JUNCEA LINES WITH A CANOLA FATTY ACID PROFILE

This application claims priority to, and hereby incorporates by reference, U.S. provisional patent application 60/987,476 filed Nov. 13, 2007.

FIELD OF THE INVENTION

The invention is in the field of *Brassica juncea* breeding, specifically relating to the development of *Brassica juncea* lines with a canola fatty acid profile using mutation breeding.

BACKGROUND

*Brassica juncea* has worldwide adaptation. It is grown as a leaf and stem vegetable and as a salad crop in the Far East and Southeast Asia. *B. juncea* is cultivated in Western Canada as a spice crop and traded as oriental or brown mustard. Due to its relatively high oil content, *B. juncea* is also grown as an oilseed crop in India, China and in south-western areas of the former Soviet Union. Most of the vegetable, spice and oilseed *B. juncea* types grown in the world are known as mustard quality as they contain high levels of glucosinolates in the meal and high levels of erucic acid in the oil fraction.

*Brassica napus* and *Brassica rapa* are two other species of *Brassica* commonly grown worldwide. Certain forms of *B. napus* and *B. rapa* are known as canola. Canola is an improved form of *B. napus* and *B. rapa*. Oilseed breeders developed low glucosinolate and low erucic acid forms of *B. napus* and *B. rapa* to improve oil and meal quality. Canola is defined by the Canola Council of Canada as containing less than 2% erucic acid content by weight and less than 30 µmoles of total glucosinolates per gram of defatted meal.

*B. juncea* has agronomic advantages over *B. napus* and *B. rapa*. *B. juncea* shows greater drought and heat tolerance than *B. napus* and *B. rapa* and has the potential to allow for the expansion of canola production into drier areas such as the southern Canadian prairies, upper Midwest of the United States and in Eastern and Western Australia (Woods, et al., 1991). *B. juncea* appears to have greater pod shattering resistance than *B. napus* and *B. rapa* which may allow for direct cutting. *B. juncea* also has different genes for blackleg (*Leptosphaeria maculans*) resistance than *B. napus* and *B. rapa* which may provide some additional resistance.

Until recently, all forms of *B. juncea* were mustard quality and could not be traded as canola. During the past twenty-five years there has been significant activity to introduce canola quality traits into *B. juncea* in an effort to change the grain quality while retaining many of the agronomic benefits of *B. juncea*.

Three distinct changes in key quality traits were required before *B. juncea* could be considered canola quality. The first change was the development of low erucic acid *B. juncea* (Kirk and Oram, 1981). The second change was the development of a low glucosinolate form of *B. juncea*. Love, et al., (1991) reported the development of a low glucosinolate form of *B. juncea* derived from an interspecific cross between *B. rapa* and *B. juncea*. Both of these publicly available sources were the first steps toward introducing canola quality traits to *B. juncea*.

The third change in quality traits required another change in fatty acid composition. While the development of zero erucic acid *B. juncea* changed the C18 fatty acid complex somewhat (Table 1), there were not enough changes to produce a *B. juncea* plant with a canola fatty acid profile. The zero erucic acid forms had too low a level of oleic acid (C18:1) and too high of levels of linoleic acid (C18:2) and linolenic acid (C18:3) to be considered comparable to canola.

TABLE 1

Comparison of fatty acid profiles of key fatty acids in various *B. napus* and *B. juncea* types - data from 2000 Canadian field trials

| Brassica type | C18:0 Stearic acid | C18:1 Oleic acid | C18:2 Linoleic acid | C18:3 Linolenic acid | C22:1 Erucic acid |
|---|---|---|---|---|---|
| Canola - *B. napus* | 1.41 | 64.72 | 18.59 | 9.53 | 0.00 |
| Canola - *B. rapa* | 1.42 | 59.92 | 20.86 | 12.45 | 0.00 |
| Mustard *B. juncea* | 0.92 | 16.37 | 20.08 | 9.85 | 38.01 |
| Zero erucic *B. juncea* | 2.67 | 44.63 | 33.92 | 11.53 | 0.00 |

Several groups began the task of changing the canola fatty acid profile in *B. juncea*. The first group based in Agriculture Canada Saskatoon has attempted the task by crossing *B. napus* to *B. juncea* in hopes of recovering a stable canola quality fatty acid profile from *B. napus*. Raney, et al., (1995) reported the transfer of the *B. napus* fatty acid profile from *B. napus* to *B. juncea* using *B. napus*, however, the authors noted that there was poor female fertility and genetic instability present in their *B. juncea* breeding lines.

Agnihotri, et al., (1995) produced crosses of *Eruca sativa* × *B. juncea* and reported an oleic acid content of 61.9%, but the glucosinolate content was approximately 104 µmoles of glucosinolates per g of meal which would be unacceptable as canola quality. This material was derived directly from a direct F1 cross, so the genetic stability was not demonstrated and there has been no subsequent published work on this project. Given the distant genetic relationship between *E. sativa* and *B. juncea*, it would be expected that there would be genetic instability and that the canola profile would be difficult to stabilize.

Applicants have also conducted interspecific crossing to transfer the canola fatty acid profile from *B. napus* and *B. rapa* to *B. juncea*. Several rounds of interspecific crossing were undertaken in an attempt to develop a canola quality fatty acid profile. Although canola fatty acid profile materials were developed, they were not stable across generations and were not repeatable across greenhouse and field environments. The plants showed effects of interspecific crossing as described by Raney, et al., (1995), including poor fertility and variation in leaf, flower and pod morphology.

Saskatchewan Wheat Pool has developed high oleic acid, low linoleic and low α-linolenic acid *B. juncea* genotypes by crossing two parental *B. juncea* lines (Potts, et al., 2001). The parental lines were not high in oleic acid or low in linoleic and linolenic acids and the authors could not provide a scientific explanation as to how the variation arose. The derived material produced an oleic acid content of greater than 55%, a linoleic acid of less than 25% and a linolenic acid content of less than 14% by weight. The source material was developed in a background of less than 30 µmoles of total glucosinolates. Potts, et al., (2001) attempted to use ethyl methane sulfonate (EMS) microspore mutagenesis to alter the C18 fatty acid complex and were not able to significantly change the fatty acid variation within the C18 complex.

The claimed source of the canola fatty acid profile was developed in a low glucosinolate *B. juncea* breeding population. Some segregants produced the canola fatty acid profile, but contained glucosinolate levels beyond the canola definition. Seed EMS mutagenesis was used in a targeted effort to alter the C18 fatty acid complex without affecting the other plant characteristics. This application discloses the development of a stable, easily identifiable source of canola fatty acid profile in B. juncea in either a canola or non-canola glucosinolate quality background.

SUMMARY OF THE INVENTION

An aspect of the invention is to provide a novel *Brassica juncea* genotype. The novel *B. juncea* genotype comprises at least 55% oleic acid by weight of total fatty acids. This invention relates to the seeds of the genotype, to plants of the genotype, to methods for reproducing the *B. juncea* genotype and uses of the genotype. The genotype can be propagated by crossing a line having this genotype with itself or another *B. juncea* plant. Another aspect of this invention is the use of seed mutagenesis to alter the C18 fatty acid complex of *B. juncea* to produce a *B. juncea* line with a canola fatty acid profile.

An aspect of the invention is to provide a method for developing a *Brassica juncea* seed having greater than about 55% oleic acid by weight of total fatty acids, comprising: mutagenizing a *Brassica juncea* cell with a mutagen; growing the mutagenized cell to produce a mutagenized plant; and selecting a seed produced from the mutagenized plant having greater than about 55% oleic acid by weight of total fatty acids.

Another aspect of the invention is to provide a *Brassica juncea* seed, or progeny seed thereof, having greater than about 55% oleic acid by weight of total fatty acid produced by the method described above. A plant or plant cell derived from this seed is also provided.

Another aspect of the invention is to provide a homogeneous assemblage of crushed *Brassica juncea* seed produced from the plant of described above, wherein the crushed *Brassica juncea* seed have an oleic acid content of greater than about 55% oleic acid by weight of total fatty acids. Another aspect is to provide the oil and meal from this seed.

Another aspect of the invention is to provide a use of a mutagen to produce *Brassica juncea* seed having greater than about 55% oleic acid by weight of total fatty acids.

Another aspect of the invention is to provide seed of *Brassica juncea* line 338, representative seed of said line having been deposited under ATCC Accession Number PTA-8533, a sub-line of 338, progeny of 338 or the sub-line, or a plant produced by crossing 338 with a second *Brassica* plant, wherein the seed has an oleic acid content greater than about 55% by weight of total fatty acids. Another aspect is to provide a *Brassica juncea* plant, or parts thereof, produced by growing this seed. Also provided is a tissue culture from this plant or seed. The plant or seed can be herbicide tolerant.

Another aspect of the invention is to provide a method of breeding a 338-derived plant comprising: obtaining the *Brassica juncea* plant, or plant parts, described above and utilizing breeding methods to produce a 338-derived plant.

Another aspect of the invention is to provide a method for producing a 338-derived *Brassica juncea* plant, or parts thereof comprising crossing the *Brassica juncea* plant, or parts thereof, described above, with a second plant to produce a first generation progeny seed; growing said first generation progeny seed to produce an F1 generation plant; optionally, repeating the steps of crossing and growing to obtain successive filial generations of said seed to obtain a 338-derived *Brassica juncea* seed, plant, or parts thereof. The plant or plant parts (including any hybrid) produced by this method is also provided.

Another aspect of the invention is to provide a method of growing *Brassica juncea* line 338, representative seed of said line having been deposited under ATCC Accession Number PTA-8533, a sub-line of 338, progeny of 338 or the sub-line, or a plant produced by crossing 338 with a second *Brassica* plant comprising: obtaining the *Brassica juncea* plant described above and growing the plant under *Brassica* plant growing conditions.

Another aspect of the invention is to provide a method of producing oil and/or meal from *Brassica juncea* line 338, representative seed of said line having been deposited under ATCC Accession Number PTA-8533, a sub-line of 338, progeny of 338 or the sub-line, or a plant produced by crossing 338 with a second *Brassica* plant comprising: growing the *Brassica juncea* plant of described above under *Brassica* plant growing conditions; harvesting the seed; and extracting oil and/or meal.

Another aspect of the invention is to provide a method of producing oil from *Brassica juncea* line 338, representative seed of said line having been deposited under ATCC Accession Number PTA-8533, a sub-line of 338, progeny of 338 or the sub-line, or a plant produced by crossing 338 with a second *Brassica* plant, comprising: crushing seeds of *Brassica juncea* line 338, representative seed of said line having been deposited under ATCC Accession Number PTA-8533, a sub-line of 338, progeny of 338 or the sub-line, or a plant produced by crossing 338 with a second *Brassica* plant; and extracting oil from said seeds.

Another aspect of the invention is to provide a population of plants produced by the method described above, said population deriving, on average, 10 to 100% of its alleles from *Brassica juncea* variety 338, representative seed of which have been deposited under ATCC Accession Number PTA-8533.

Another aspect of the invention is to provide a use of *Brassica juncea* variety 338, representative seed of which have been deposited under ATCC Accession Number PTA-8533, a sub-line of 338, progeny of 338 or the sub-line, or a plant produced by crossing 338 with a second *Brassica* plant, for breeding, for growing a plant and/or for oil and/or meal production.

Another aspect of the invention is to provide seed of *Brassica juncea* line 1629, a sub-line of 1629, progeny of 1629 or the sub-line, or a plant produced by crossing 1629 with a second *Brassica* plant, wherein the seed has an oleic acid content greater than about 55% by weight of total fatty acids. The plant produced from this seed is also provided. The plant or seed may be tolerant to a herbicide.

Another aspect of the invention is to provide a method for producing a 1629-derived *Brassica juncea* plant, or parts thereof comprising: crossing the *Brassica juncea* plant, or parts thereof, described above with a second plant to produce a first generation progeny seed; growing said first generation progeny seed to produce an F1 generation plant; optionally, repeating the steps of crossing and growing to obtain successive filial generations of said seed to obtain a 1629-derived *Brassica juncea* seed, plant, or parts thereof.

Another aspect of the invention is to provide a use of *Brassica juncea* variety 1629, a sub-line of 1629, progeny of 1629 or the sub-line, or a plant produced by crossing 1629 with a second *Brassica* plant, for breeding, for growing a plant and/or for oil and/or meal production.

Another aspect of the invention is to provide seed of *Brassica juncea* line 2397, a sub-line of 2397, progeny of 2397 or the sub-line, or a plant produced by crossing 2397 with a second *Brassica* plant, wherein the seed has an oleic acid content greater than about 55% by weight of total fatty acids. Also included is a plant or plant part produced by growing this seed. The plant or seed may be tolerant to a herbicide.

Also provided is a method for producing a 2397-derived *Brassica juncea* plant, or parts thereof comprising: crossing the *Brassica juncea* plant, or parts thereof, described above, with a second plant to produce a first generation progeny seed; growing said first generation progeny seed to produce an F1 generation plant; and optionally, repeating the steps of crossing and growing to obtain successive filial generations of said seed to obtain a 2397-derived *Brassica juncea* seed, plant, or parts thereof.

Another aspect of the invention is to provide a use of *Brassica juncea* variety 2397, a sub-line of 2397, progeny of 2397 or the sub-line, or a plant produced by crossing 2397 with a second *Brassica* plant, for breeding, for growing a plant and/or for oil and/or meal production.

Another aspect of the invention is to provide a *Brassica juncea* seed comprising an oleic acid content of 55% or greater and a linolenic acid contents of 8% or less. The oleic acid content can be 60% or 65%. A *Brassica juncea* seed comprising 65% oleic acid or greater and a linolenic content of 8% or less is also provide. A plant and oil derived from this seed is provided.

DEFINITIONS

In the description and tables which follow a number of terms are used. In order to aid in a clear and consistent understanding of the specification the following definitions and evaluation criteria are provided.

"Canola" is defined by the Canola Council of Canada as "an oil that must contain less than 2% erucic acid, and the solid component of the seed must contain less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil-free solid".

"Fatty acid composition" is the typical percentages by weight of fatty acids present in the endogenously formed oil of the mature whole dried seeds calculated as percent by weight of total fatty acid. Typically, during determination of the fatty acid composition, the seeds are crushed and are extracted as fatty acid methyl esters following reaction with methanol and sodium methoxide. The resulting ester is analyzed for fatty acid content by gas liquid chromatography using a capillary column which allows separation on the basis of the degree of unsaturation and fatty acid chain length. This procedure is described in the work of Daun, et al., (1983) *J. Amer. Oil Chem. Soc.* 60:1751-1754 which is herein incorporated by reference. Other methods of detecting and measuring fatty acid composition are known to those skilled in the art.

"Glucosinolate Content" is the total glucosinolates of seed at 8.5% moisture expressed in micromoles per gram. Typically, total glucosinolates are measured according to the American Oil Chemists' Society (AOCS) Official Method AK-1-92 (Determination of glucosinolates content in rapeseed—colza by HPLC). Capillary gas chromatography of the trimethylsityl derivatives of extracted and purified desulfoglucosinolates with optimization to obtain optimum indole glucosinolate detection as described in *"Procedures of the Western Canada Canola/Rapeseed Recommending Committee Incorporated for the Evaluation and Recommendation for Registration of Canola/Rapeseed Candidate Cultivars in Western Canada"*. Other methods of detecting and measuring glucosinolates are known to those skilled in the art.

"Half-seed analysis" is a procedure whereby fatty acid analysis is carried out on one of the two cotyledons (half-seed) and the remaining seedling carrying the second cotyledon forms a plant.

"Line" is a homogeneous assemblage of plants carrying substantially the same genetic material.

"Oil content" is the typical percentage by weight oil present in the mature whole dried seeds is determined by methods based on "AOCS Official Method Am 2-92 Oil content in Oilseeds". Analysis by pulsed Nuclear Magnetic Resonance (NMR) "ISO 10565: 1993 Oilseeds Simultaneous determination of oil and water—Pulsed NMR method" or by NIR (Near Infra Red Spectroscopy) (Williams, 'Application of Near Infrared Reflectance Spectroscopy to Analysis of Cereal Grains and Oilseeds', *Cereal Chem.* 52:561-576 (1975), herein incorporated by reference) are acceptable methods and data may be used for Canadian registration as long as the instruments are calibrated and certified by Grain Research Laboratory of Canada. Other methods as known to those skilled in the art may also be used. Percent oil is calculated as the weight of the oil divided by the weight of the seed at 0% moisture.

"Protein content" is the typical percentage by weight of protein in the oil free meal of the mature whole dried seeds is determined by methods based on "AOCS Official Method Ba 4e-93 Combustion Method for the Determination of Crude Protein". Protein can be analyzed using NIR (Near Infra Red Spectroscopy), (Williams, 'Application of Near Infrared Reflectance Spectroscopy to Analysis of Cereal Grains and Oilseeds', *Cereal Chem.* 52:561-576 (1975), herein incorporated by reference) Data can be used for Canadian registration as long as the instruments are calibrated and certified by Grain Research Laboratory of Canada. Other methods known to those skilled in the art may also be used.

"Thousand kernel weight" (TKW) is defined as the weight (g) of 1000 seeds of a particular line or variety. This is a method of assessing seed size; the larger the seed size, the greater the TKW value.

"Total saturates" is the combined percentage of palmitic (C16:0), stearic (C18:0), arachidic (C20:0) and behenic (C22:0) fatty acids. The fatty acid concentrations are determine in accordance with the standard procedure, American Oilseed Chemists' Society (AOCS) method Celd-91 (the disclosure of which is incorporated herein by reference). Fatty acid concentrations are expressed as a percentage by weight of total fatty acid content.

"Variety" or "cultivar" is a line that is used for commercial production.

"Canola fatty acid profile" means a fatty acid profile comprising between approximately 0.8% to 3.0% C18:0, 51.0% to 70.0% C18:1; 15.0% to 30.0% C18:2, 5.0% to 14.0% C18:3, and 0% to 2% C22:1 as per the Codex Alimentaris Vol 8, 2001. The Canola Council of Canada officially lists canola oil as containing less than 2% erucic acid. All values are approximate as there is some fluctuation in fatty acid composition due to environmental conditions. Values are expressed as percent by weight of total fatty acid.

DESCRIPTION OF THE DRAWINGS

FIG. 9. Flow diagram of the methods used to produce *B. juncea* lines with a canola fatty acid profile.

DESCRIPTION OF THE VARIOUS EMBODIMENTS

Figure 1:
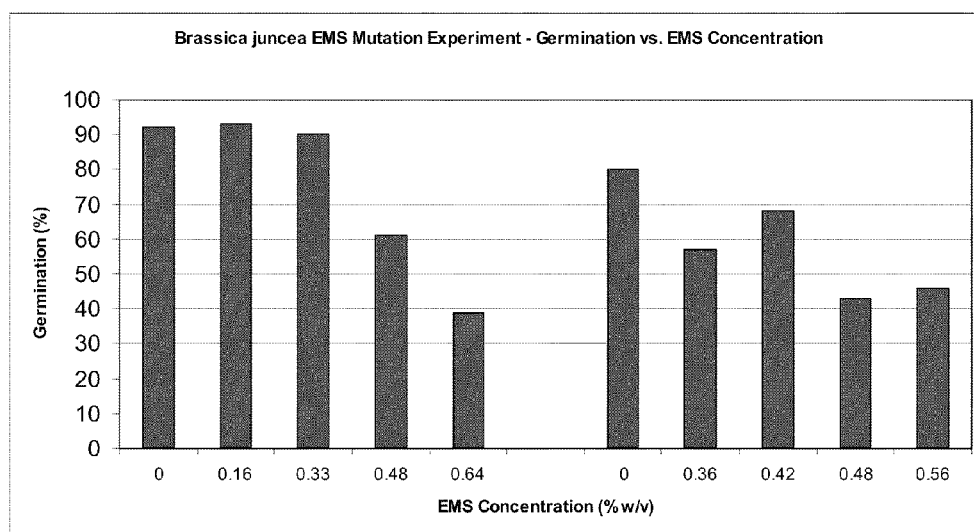
FIG. 1. EMS kill curves of *B. juncea* seed treated with various concentrations of EMS.

*B. juncea* genotypes having a canola fatty acid profile were developed using ethyl methane sulfonate (EMS) seed mutagenesis. These lines have a low erucic acid content and have an increased level of oleic acid, which results in an oil profile similar to that of *B. napus* canola. The lines were produced by seed mutagenesis followed by rigorous selection for the high oleic acid trait. Three lines were selected from the new genotypes and designated 338, 1629 and 2397. The 338 line has been deposited with American Type Culture Collection (ATCC) Manassas, Va. 20110-2209 USA under accession number PTA-8533 on Jul. 13, 2007.

The new lines were developed by mutation breeding, followed by rigorous selection for the high oleic acid trait. Mutation breeding is a valuable tool to induce variation in a species where that variation does not exist. For example, the canola fatty acid profile does not appear to exist in native *B. juncea* and therefore the variation was developed by significant technical intervention by man.

Mutation breeding has been used to improve fatty acid composition in *Brassica* breeding. Velasco, et al., (1997) conducted their experiment of *B. carinata*—a relative of *B. juncea* and *B. napus*. The starting material was high in erucic acid content—(approximately 40%) and they worked to reduce the erucic, linoleic and linolenic acid contents. They used 1.0% (vol/vol) ethyl methane sulfonate (EMS) to induce the mutations and harvested 1011 M1 plants in their experiment. They then evaluated 8331 plants from the next (M2) generation and selected M3 seed to continue evaluation. 40 to 70 M3 plants were evaluated from each M2 plant and continued the effort to evaluate 30 to 70 M4 plants from each M3 line. M5 seed was evaluated using the half-seed technique. The authors noted that they produced several lines with low erucic acid content and noted some improvement in linolenic acid content. Despite huge populations, there were few differences produced in the oleic acid content in their experiment.

Potts, et al., (U.S. Pat. No. 6,303,849) reported using EMS microspore mutation to induce changes in saturated fatty acid composition. They indicated that they successfully produced a lower saturated fatty acid *B. juncea*, but no details were provided as to methodology or stability of the changes in fatty acid composition.

Numerous mutagens can be used to induce mutations in the DNA of a plant. As is known to those skilled in the art, mutagens that can be used include: ethylmethane sulfonate (EMS), ethylnitrosourea (ENU), neutrons, UV rays, γ-irradiation, x-ray, transposon induced-mutagenesis, and genetic insertion mutagenesis, for example, T-DNA insertion mutagenesis. Although the applicants' teaching uses EMS, it is to be understood that the invention is not limited to EMS, but includes any mutagen that induces mutations in plant cells. Further, any cell can be mutagenized. The mutagenized cell should give rise to a plant, for example, by germination or regeneration. For example, seed, protoplasts, microspores, cells, explants, calli, embryos, can all be mutagenized and give rise to plants. Although the applicant mutagenized seed in developing the high oleic trait in *B. juncea*, it is to be understood that the invention includes mutagenesis of any plant cell, followed by regeneration or germination of a plant.

The applicants' teachings include the specific lines disclosed herein which carry the high oleic acid trait. The applicant's teachings also include methods to allow the skilled worker to develop additional new lines than those specifically disclosed here with similar traits. Accordingly, the applicants' teaching is not restricted to the specific lines disclosed herein, but any lines carrying similar traits developed by the methods disclosed in the invention.

The combination of *B. juncea* plant type and agronomic performance with a canola-like fatty acid profile enables canola production in drought and heat-prone areas.

The applicants' teachings also include progeny and descendents of these new *B. juncea* lines. The progeny or descendents can be developed by methods of breeding and/or tissue culture as are known to those skilled in the art. For example, the progeny or descendents can contain the canola fatty acid profile developed in these lines. Accordingly, the descendents or progeny can have any number of genes from the developed lines. The descendents or progeny can include only those genes that provide the canola fatty acid phenotype, or additional genes. This can be determined by molecular analysis as is known to those skilled in the art.

Also provided is a homogeneous assemblage of crushed *Brassica juncea* seed disclosed herein, or a homogeneous assemblage of crushed *B. juncea* seed from a progeny or descendent, wherein the crushed *Brassica juncea* seed have an oleic acid content of greater than about 55% oleic acid by weight of total fatty acids. Also provided is the oil and meal from this seed.

Also provided is a method of producing oil from the new *Brassica juncea* lines, a sub-line of these lines, progeny of these lines or sub-lines, or a plant produced by crossing these lines with a second *Brassica* plant, comprising: crushing seeds of the new line (or progeny, sublines or plant produced by crossing these new lines with a second *Brassica* plant); and extracting oil from said seeds. Optionally, the method can further comprise the step of refining, bleaching and deodorizing said oil.

EXPERIMENTS

Experiment 1

Establishing Kill Curves for *B. juncea* Seed Mutagenized with Various Concentrations of Ethyl Methane Sulfonate (EMS)

A bulk population (99SJ-1309) was created for this experiment from 8 different low glucosinolate and low erucic acid *B. juncea* breeding lines. These lines were selected for a range of quality and agronomic traits such as oil content and seed size. 500 seeds of the bulk population were used for each treatment of the following experiment. The seeds were soaked in various concentrations EMS for 18 hours and then washed 3 times. A sub-sample of 100 seeds was placed in a germination box at 25° C. for 7 days. After 7 days, the number of seeds that germinated and produced a healthy radicle was calculated. All seeds that were treated with EMS took at least 2 days longer to germinate than controls.

EMS treatment of seed affected the germination rate (FIG. 1, Table 2 and Table 3). At the lowest concentrations (0.16 and 0.33%), there was little effect on germination rate, however at the highest concentrations of EMS, germination rates were less than 50% (Table 2 and Table 3). This experiment was not replicated. Its purpose was to evaluate the effect of EMS on seed germination rate. The first experiment was designed to test a broad range of EMS application rates and the second experiment was to reduce the range of EMS treatment to develop the desirable mutations (Table 3). The 0.36% EMS treatment rate resulted in a much lower germination rate than expected.

TABLE 2

EMS kill curve # 1
Treatment 1

| EMS w/v | 0% | 0.16% | 0.33% | 0.48% | 0.64% |
|---|---|---|---|---|---|
| conc. in 25 ml | 0 | 32.5 µl | 70 µl | 102.5 µl | 135 µl |
| % germination | 92 | 93 | 90 | 61 | 39 |

TABLE 3

EMS kill curve # 2
Treatment 2

| EMS w/v | 0% | 0.36% | 0.42% | 0.48% | 0.56% |
|---|---|---|---|---|---|
| Conc. in 25 ml | 0 | 76 µl | 89 µl | 102.5 µl | 118.75 µl |
| % germination | 80 | 57 | 68 | 43 | 46 |

Experiment 2

Development of a Population of *B. juncea* Mutagenized Seed and Analysis of Seed Harvested from Plants Derived from the Mutagenized Seed The goal was to use EMS seed mutagenesis to alter the C18 fatty acid complex of *B. juncea* to produce a minimum of 55% oleic acid content. A bulk population (coded 99SJ-1309) was produced for this experiment. The bulk was produced from 8 different *B. juncea* breeding lines (Table 4) selected for a range of quality traits such as oil content, protein content and agronomic traits such as thousand kernel weight (TKW). All of the lines were low in glucosinolate content and also were low in erucic acid content. Although the lines used in the bulk population were proprietary breeding lines, they were representative of publicly available low oleic acid *B. juncea* breeding material available at the time.

TABLE 4

Eight proprietary *B. juncea* breeding lines used to develop the original population that was used in the mutation breeding experiment.

| Variety | % Oil | % Protein | Total gluc µmol/gram | % Green seed | % Germ | Thousand seed weight (g) |
|---|---|---|---|---|---|---|
| 98SJ-3880 | 49.16 | 20.59 | 2.23 | 5 | 95 | 2.582 |
| 98SJ-3973 | 49.16 | 23.19 | 0.53 | 3 | 97 | 2.594 |
| 98SJ-4045 | 49.65 | 21.49 | 4.16 | 13 | 87 | 2.920 |
| 98SJ-3970 | 50.05 | 21.52 | 7.32 | 16 | 84 | 2.684 |
| 98SJ-3994 | 50.26 | 21.36 | 2.16 | 0 | 100 | 3.004 |
| 98SJ-4032 | 49.05 | 24.18 | 1.99 | 0 | 100 | 2.792 |

TABLE 4-continued

Eight proprietary *B. juncea* breeding lines used to develop the original population that was used in the mutation breeding experiment.

| Variety | % Oil | % Protein | Total gluc µmol/gram | % Green seed | % Germ | Thousand seed weight (g) |
|---|---|---|---|---|---|---|
| 98SJ-4080 | 49.36 | 23.21 | 11.42 | 3 | 97 | 2.448 |
| 98SJ-4088 | 51.82 | 22.29 | 6.12 | 4 | 96 | 2.632 |

The mutation breeding experiment was carried out by treating approximately 560 g of seed of 99SJ-1309 with a 0.33% w/v solution of EMS.

There were several reasons why a low concentration of EMS was chosen for the experiment. The first reason was to minimize the probability of massive genetic mutations which could cause too many phenotypic abnormalities in the resulting population. The goal was to grow this material in a field experiment. Very high levels of EMS might induce the desirable fatty acid changes, but might also induce substantial changes in phenotype resulting in plants with too many abnormalities. The second reason why the low level of mutagen was used was that the fatty acid profile changes are accurately detectable using gas-chromatograph technology, therefore it would be possible to screen a large population and to identify any change in fatty acid composition.

Seed was incubated in EMS in the dark at 20° C. for 18 hours. At the end of the treatment period, the mutagenized seed was rinsed three times with distilled water. The seed was planted in an isolated field on May 19, 1999. The population was allowed to produce open-pollinated seed. The plants were not self-pollinated because the self-pollination bags, used to prevent non-self pollen from fertilizing the flowers, have been known to affect fatty acid profile which could increase the occurrence of false positives. 6403 single plants were harvested from the field along with several *B. napus* check plants.

Each plant was threshed, placed in an envelope and sent to Georgetown, Ontario to assess the fatty acid composition using a gas chromatograph. Fatty acid analysis was conducted using samples from individual plants using a standard protocol. Approximately 25-30 individual seed were placed in a glass tube and crushed with a steel rod. Then 1.2 mls of n-hexane was added and shaken for approximately 10-15 seconds and was allowed to rest for 15 minutes. Next, 0.2 ml of 0.5N sodium methoxide was added to the glass tube, shaken for 10-15 seconds and allowed to sit for 15 minutes. Finally, 2 ml of 0.3% acetic acid solution was added and the tube was allowed to rest for 1 hour. The top layer of the methyl ester solution was transferred into a gas chromatograph vial and run through the gas chromatograph.

Figure 2:
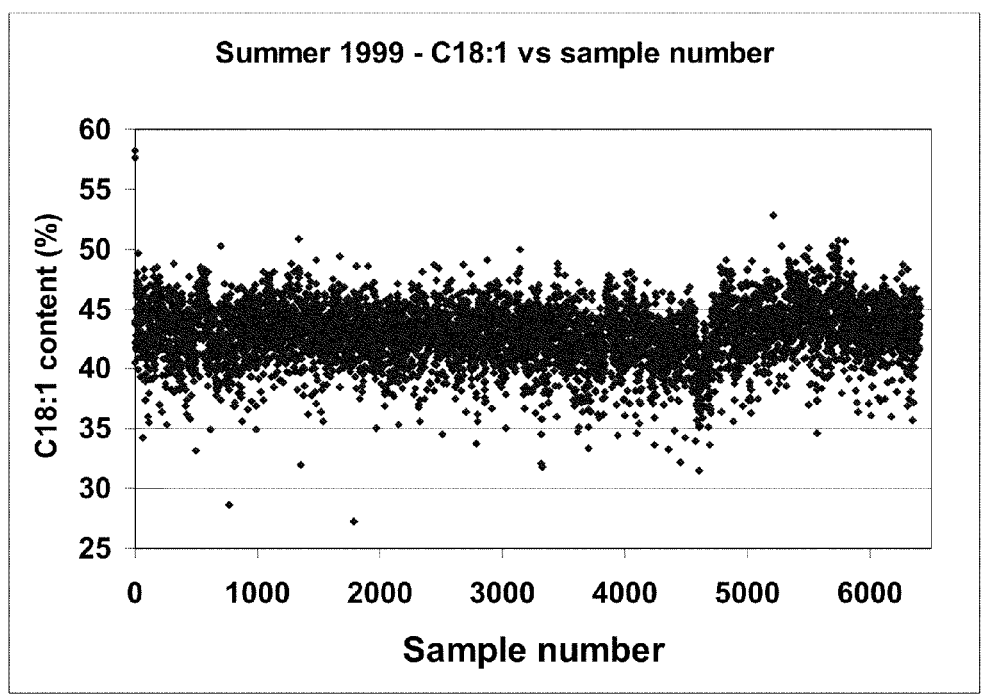
FIG. 2. Percent oleic acid content in an EMS-mutagenized population of *B. juncea* harvested in the fall of 1999

A total of 6403 breeding lines were evaluated for oleic acid content in the first cycle of the project (FIG. 2). None of the breeding lines met the selection criterion of 55% oleic acid content. However, the seed from several of the open-pollinated plants produced oleic acid content levels of between 50 and 55% (Table 5). Levels greater than 50% oleic acid were considered an improvement over the traditional oleic acid composition of low erucic acid *B. juncea* (Table 1). There was a small shift in C18:2 to C18:1 in the fatty acid profile (Table 5), as compared to the traditional low oleic acid *B. juncea* lines (Table 1). However, a greater shift in C18:2 to C18:1 was required to achieve the desired C18:1 level found in *B. napus* canola.

TABLE 5

B. juncea lines developed during the summer of
1999 with greater than 50% oleic acid content

| B. juncea Line | C18:0 | C18:1 | C18:2 | C18:3 |
|---|---|---|---|---|
| 5208 | 1.69 | 52.83 | 23.81 | 15.65 |
| 1341 | 2.03 | 50.81 | 26.38 | 14.57 |
| 703 | 1.80 | 50.26 | 26.52 | 15.72 |
| 5498 | 1.94 | 50.07 | 27.31 | 14.75 |
| 5726 | 1.85 | 50.18 | 27.31 | 14.91 |
| 5743 | 2.40 | 50.75 | 27.35 | 13.71 |
| 5275 | 1.73 | 50.26 | 27.45 | 14.65 |
| 5728 | 2.17 | 50.05 | 27.85 | 14.17 |
| 5697 | 2.00 | 50.23 | 28.13 | 13.71 |
| 5799 | 1.94 | 50.64 | 28.56 | 13.23 |

Figure 3:
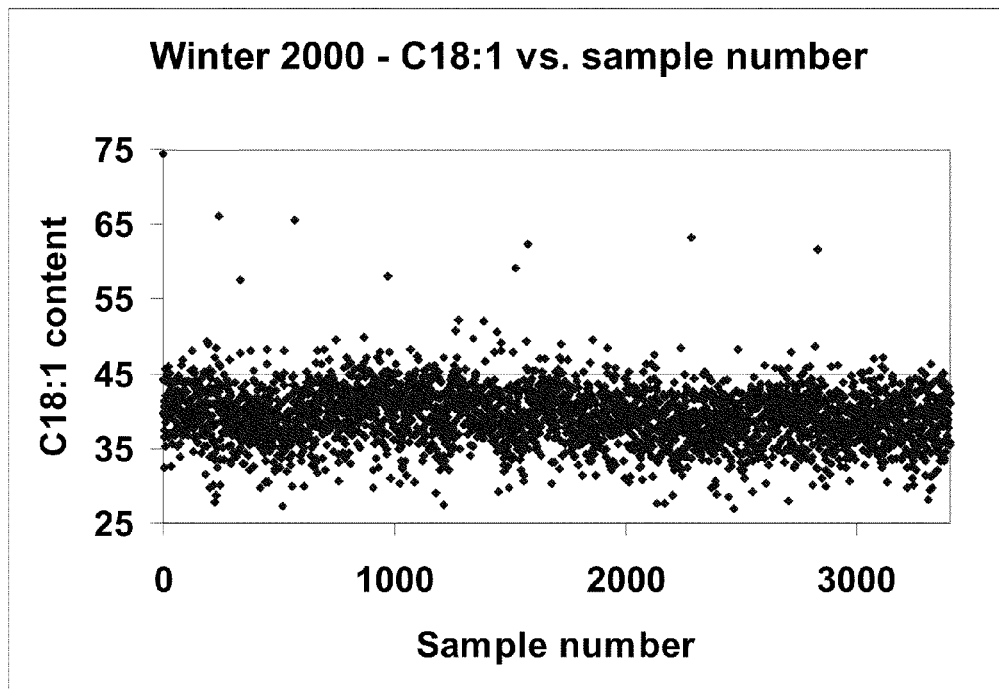
FIG. 3. Percent oleic acid content in an EMS-mutagenized population of *B. juncea* harvested in the spring of 2000

Despite the success in increasing the oleic acid content to 50% in the summer 1999 experiment, B. juncea lines with oleic acid content close to 60% were needed to consider them equivalent to a canola fatty acid profile. After the 1999 summer experiment, a new bulk was created, coded as 00SJ-0466 using the 500 lines from the mutagenized population that had the highest oleic acid content identified in the summer 1999 experiment. The experimental protocol for the fall 1999 experiment was similar to the summer 1999 experiment, but the EMS mutagen rate was increased to 0.48% to induce further genetic mutations. As shown in Experiment 1, 0.48% EMS reduced the germination rate to approximately 50%. Approximately 500 g of mutagenized seed was planted in a field near Puerto Vallarta, Mexico where the B. juncea plants were allowed to open-pollinate. A total of 3599 open-pollinated B. juncea plants were harvested, threshed and seed sent to the Georgetown, Ontario lab for whole seed analysis. Twelve lines were identified as having greater than 50% oleic acid content, and eight of these had greater than 55% oleic acid (see FIG. 3 and Table 6). A change in the C18 fatty acid complex was observed as an increase in oleic acid and decreases in linoleic acid and linolenic acids as compared to the original mutagenized population (Table 6). Several of the sources, 2397, 2787 and 1060, produced linolenic acid (C18:3) content of below 10% (and even below 8%). These sources are extremely low in linolenic acid as compared to previously reported in B. juncea (Potts, et al., 2001). The lowest linolenic acid content reported in Potts, et al., (2001) was 9.4%. Raney, et al., (1995) reported C18:3 levels as low as 4.7%, but these sources were not in a 100% B. juncea background as they were derived from crosses of B. juncea×B. napus and were showing effects of interspecific crossing. Accordingly, the present lines have a lower level of C18:3 compared to Potts, et al., (2001).

TABLE 6

B. juncea lines derived from the 1999-2000 experiment in Puerto Vallarta,
Mexico producing oleic acid content of greater than 50%.

| VARIETY | SOURCE | C18:0 | C18:1 | C18:2 | C18:3 |
|---|---|---|---|---|---|
| 00SJ-5256 | 5 | 1.99 | 50.79 | 26.23 | 14.77 |
| 00SJ-5270 | 20 | 2.02 | 52.24 | 26.32 | 13.26 |
| 00SJ-5382 | 144 | 1.63 | 52 | 26.47 | 13.6 |
| 00SJ-5436 | 202 | 2.12 | 50.58 | 24.78 | 15.35 |
| 00SJ-5518 | 286 | 1.78 | 59.19 | 18.77 | 13.99 |
| 00SJ-5569 | 338 | 1.67 | 62.45 | 16.59 | 12.96 |
| 00SJ-6277 | 1060 | 1.91 | 63.19 | 20.68 | 7.71 |
| 00SJ-6828 | 1629 | 1.65 | 61.74 | 21.49 | 7.97 |
| 00SJ-4231 | 2397 | 1.84 | 66.12 | 19.79 | 5.54 |
| 00SJ-4327 | 2529 | 2.22 | 57.54 | 25.73 | 7.25 |
| 00SJ-4561 | 2787 | 1.69 | 65.49 | 19.49 | 7.25 |
| 00SJ-4964 | 3242 | 1.75 | 58.18 | 21.56 | 12.83 |

Experiment 3

Stability of Fatty Acid Composition

The fatty acid profile of individual seeds was evaluated using a technique called half-seed analysis. Half-seed analysis was performed as follows: Single seeds were allowed to germinate for 2 or 3 days. The outer cotyledon was placed in a vial for sample analysis and the remaining seedling was transplanted in a known position to facilitate cross referencing. The sample preparation and run for the fatty acid analysis for the half seed was similar to the whole seed protocol described above.

After the identification of the 8 lines that had greater than 55% oleic acid content in Mexico, experiments were conducted to confirm the stability of the fatty acid composition. During the spring of 2000, half-seed analysis was conducted to verify the relationship between oleic acid content of an open-pollinated seed and the fatty acid profile of seed produced on individual plants.

Several of the eight high oleic acid lines above were discarded based on seed amount produced on the original mother plant and oleic acid level (Table 6). Sources 5, 20, 144, 202 were discarded from the rest of the experiments due to the relatively low oleic acid content value as compared to other lines identified at the same time (286, 338, 1060, 1629, 2397, 2529 2787 and 3242).

The plants were categorized as high (>60% oleic acid), moderately high (55 to 60% oleic acid), moderately low (50-55% oleic acid) and low (<50% oleic acid) for each source. The four categories are plotted against frequency of individuals from each source in FIG. 4.

Figure 4:
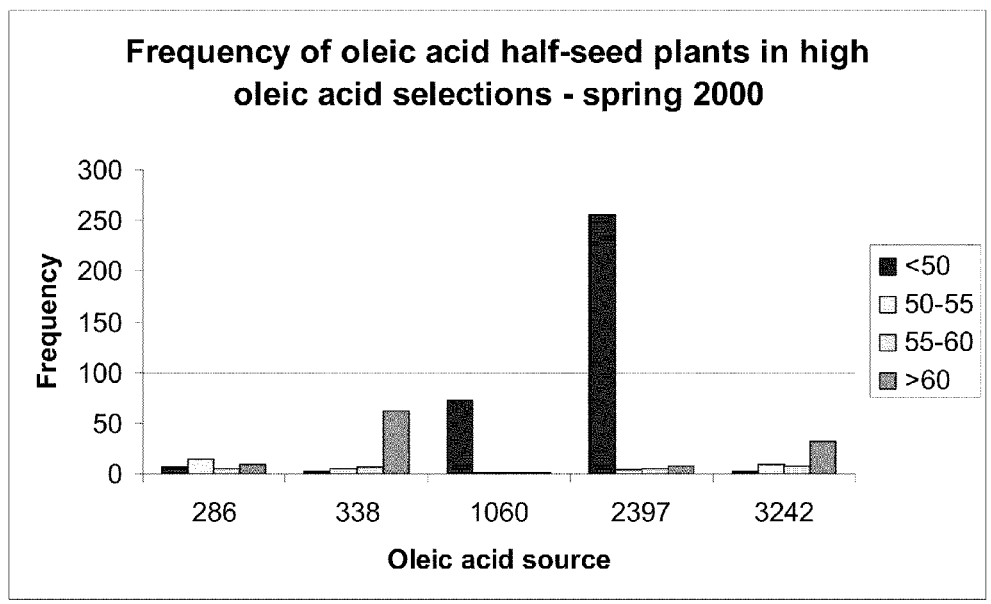
FIG. 4. Frequency of oleic acid content of half-seed fatty acid profile from high oleic acid open-pollinated plants identified in the spring of 2000.

Variable numbers of half-seed results were generated based on seed availability. Several sources, such as 1060 and 2397, produced very few high oleic acid individuals (FIG. 4) despite being identified as high oleic acid content based on seed harvested from the Mexico experiment. These two sources did produce some individuals with high oleic acid segregates, but the proportion of individuals greater than 55% oleic acid was very low. This demonstrates the potential instability of identifying stable high oleic acid plants. The 286, 338 and 3242 sources produced a larger number of individuals with high oleic acid content. These three sources showed a reasonable relationship between the whole seed fatty acid value and the frequency of high oleic acid cotyledons (FIG. 4). None of the evaluated sources produced a pure source of all high oleic acid cotyledons, showing continued segregation under open-pollinated conditions and the early instability of the canola fatty acid profile.

Figure 5:
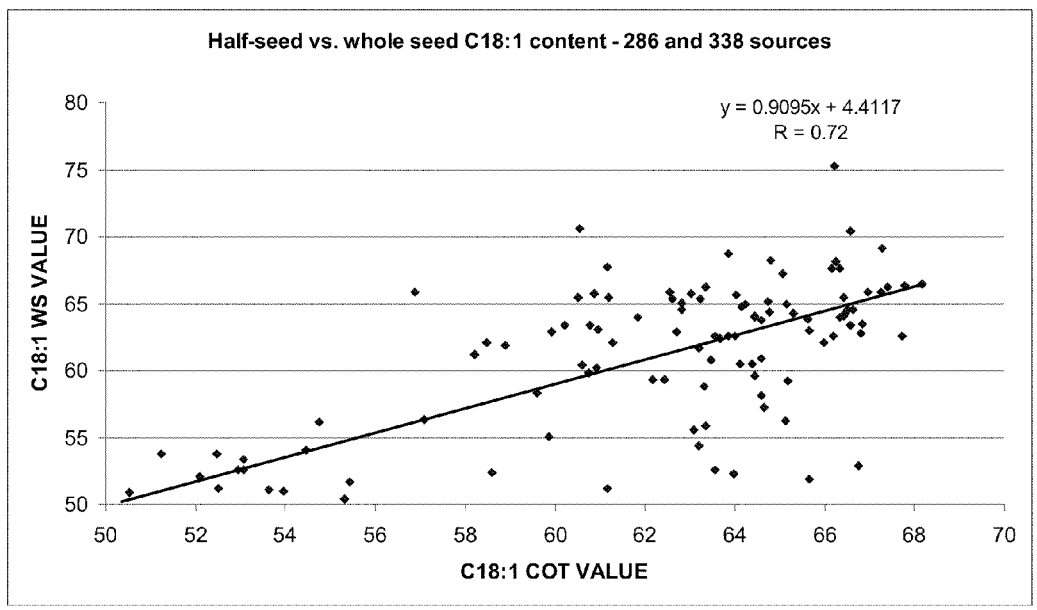
FIG. 5. Half-seed vs. whole seed C18:1 content for the 286 and 338 sources comparing individual cotyledon oleic acid content with whole seed from the self-pollinated resultant plant.

As a means of evaluating stability, the 338 and 286 sources were tested to demonstrate the relationship between a parent plant and its seed. Seed harvested from the original Mexico-derived plants was screened using half-seed analysis and all seed with less than 50% oleic acid was discarded. The remaining plants were allowed to self-pollinate in the greenhouse and the self pollinated seed produced on the plants was harvested individually. Seed was analyzed to determine whether there was a relationship between half-seed fatty acid profile of the parent plant and the whole seed fatty acid profile of the self-pollinated seed. 113 individuals were examined for half-seed and whole seed fatty acid profile and the data are shown in FIG. 5.

There was good stability from half-seed to whole seed fatty acid profile. Individuals with the highest oleic acid content tended to produce seed with a greater proportion having high oleic acid content; individuals with low oleic acid content continued to produce seed with low oleic acid content. This meant that there was a stable, predictable inheritance to the canola fatty acid profile in B. juncea.

This experiment was taken one step further to evaluate the multi-generational stability of the fatty acid profile. Seed from the original plants harvested in Mexico was compared to the seed derived from 73 of the selections from the above experiment. Accordingly, the individual oleic acid from the parent was compared to the whole seed of the child and the individual seeds of the grandchildren. This was done to determine whether a high oleic acid seed would give rise to a high oleic acid plant and in turn produce seed that was high in oleic acid. In the fall of 2000, whole seeds from 73 individuals were examined from the 286 and 338 sources. Thirty-six seed from each of the 73 self pollinated plants were evaluated for half seed analysis and the mean cotyledon fatty acid profile was compared to the original cotyledon oleic acid from the Mexico-derived seed in an effort to examine stability.

Figure 6:
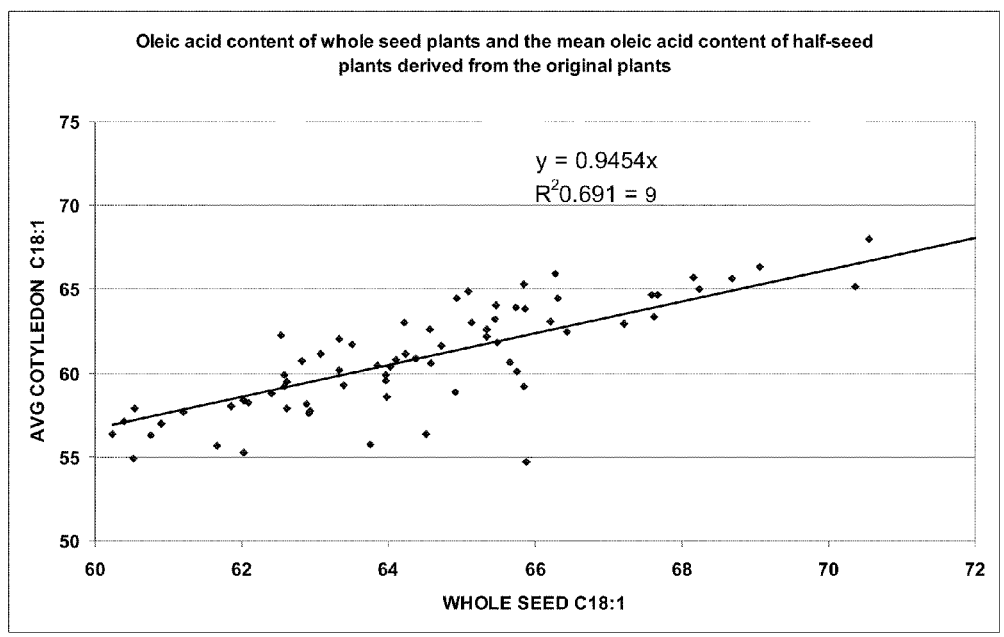
FIG. 6. Comparison of 73 individual whole seed oleic acid value and the resulting half-seed oleic acid level.

There was a good relationship between the whole seed value and the mean half-seed oleic acid level of the resulting seed (FIG. 6). It appeared that some families were fixed for the high oleic acid trait and others continued to segregate. Of the 73 families, 23 were fixed for high oleic acid. The other families appeared to be segregating and since cotyledons were selected that were greater than 50% oleic acid, there were no low oleic acid families isolated. All of these 73 lines were evaluated in field experiments during the summer of 2001.

Demonstrating greenhouse stability was a useful first experiment, but it was desirable to demonstrate field stability of the fatty acid composition in the summer of 2000. The 338 and 1629 oleic acid sources were grown in a field near Rosetown, Saskatchewan (SK). Both the 338 and 1629 sources produced oleic acid content of greater than 55%, indicating that the canola fatty acid profile could be produced in a Canadian field (Table 7).

Experiment 4

Inheritance Studies

Figure 7:
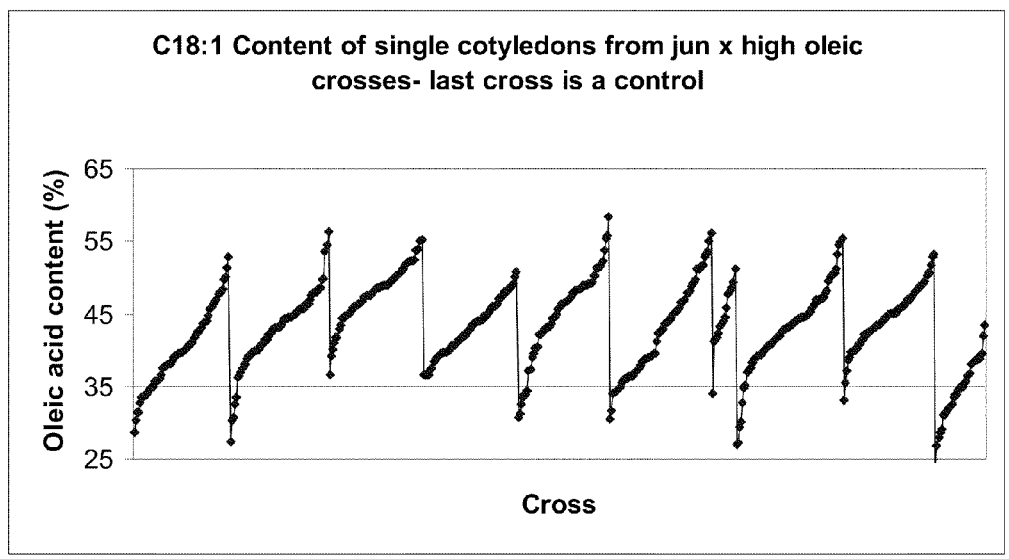
FIG. 7. Oleic acid content of high oleic×low oleic F1 cotyledons. The last cross represents a low oleic acid control.

A new experiment was initiated to assess the inheritance of high oleic acid. After the isolation of 338 oleic acid source lines in the spring of 2000, 8 crosses were made using a series of low oleic acid B. juncea breeding lines and canola fatty acid sources. If the trait were dominant, then individuals crossed from high oleic to low oleic acid would all have high oleic acid content. If the trait were recessive, there would be no F1 seed that was high oleic acid content. All of the F1's were intermediate between the low and high oleic acid parents (FIG. 7). At the F1 level, it appeared as though the high oleic acid trait was either recessive or co-dominant.

Figure 8:
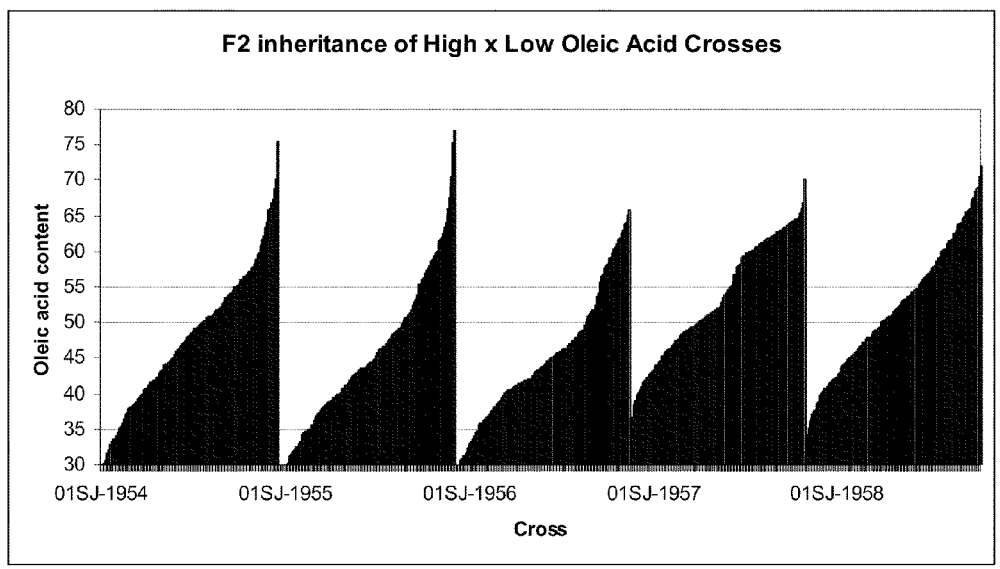
FIG. 8: F2 segregation of 5 high oleic×low oleic acid crosses evaluated in the winter of 2001.

Once the F1's were grown, each F2 was harvested. Five different F2 populations were evaluated for fatty acid profile as up to 300 single cotyledons were evaluated from each cross in project SJ-179 during the winter of 2001 (FIG. 8).

TABLE 8

Segregation ratios within each F2 population of high, moderate and low oleic acid B.juncea plants from SJ-179.

| Cross | <50 | 50-55 | 55-60 | >60 | Total | Chi-square |
|---|---|---|---|---|---|---|
| 01SJ-1954 | 166 | 55 | 40 | 27 | 288 | 0.34 |
| 01SJ-1955 | 205 | 26 | 31 | 26 | 288 | 3.55 |
| 01SJ-1956 | 216 | 22 | 23 | 26 | 287 | 2.34 |
| 01SJ-1957 | 110 | 56 | 32 | 87 | 285 | 30.06*** |
| 01SJ-1958 | 125 | 62 | 36 | 64 | 287 | 10.88*** |

***Represents significance at 0.001 level

Table 8 shows the results from categorizing high oleic acid individuals as greater than 55% oleic acid. Three of the crosses showed a good fit with a Chi-square distribution and two crosses show significant differences at the 0.001 level. The assumption was that the mutation(s) would be recessive, but in fact the mutation(s) were found to be recessive in only 3 of the 5 crosses. In the case of the other 2 crosses, the mutation(s) show a different type of inheritance pattern in the F2 generation. It is entirely likely that the last two crosses contain some modifier genes that caused a different distribution of fatty acid composition.

TABLE 7

Field stability of 338 and 1629 oleic acid sources of B. juncea

| SOURCE | C16:0 | C18:0 | C18:1 | C18:2 | C18:3 | C20:0 | C20:1 | C22:0 | C22:1 | C24:0 |
|---|---|---|---|---|---|---|---|---|---|---|
| JS0350 | 3.57 | 1.67 | 43.32 | 33.57 | 15.72 | 0.47 | 1.20 | 0.25 | 0.04 | 0.19 |
| 338 | 3.84 | 2.07 | 63.50 | 16.06 | 11.70 | 0.65 | 1.46 | 0.32 | 0.06 | 0.35 |
| 1629 | 3.66 | 2.22 | 66.73 | 13.55 | 10.84 | 0.72 | 1.48 | 0.37 | 0.05 | 0.38 |
| B. rapa | 3.84 | 1.01 | 58.13 | 19.74 | 10.01 | 1.03 | 1.98 | 1.07 | 2.11 | 1.08 |

Based on preliminary experiments in Rosetown, SK during the 2000 field season, several 338-derived breeding lines in project SJ-179 were advanced and sent to Chile in the fall of 2000 for a seed increase to conduct multi-location yield trial assessments during 2001.

The highest oleic acid plants from this project were self pollinated and used in another round of crossing to low oleic acid B. juncea lines in project SJ-196. The F1's were created and evaluated in the next project—SJ-210. Once again, the F1's created from high×low oleic acid crosses were moderate oleic acid content—i.e., only 1 of the 216 individuals produced an oleic acid content of greater than 55% (Table 9).

This again indicates either a co-dominant or recessive trait. Given that some of the crosses had a higher number of individuals with greater than 50% oleic acid content, it is likely that some modifiers contribute to the oleic acid content. This second round of crossing of high×low oleic acid content using high oleic acid individuals may be selecting for modifier gene accumulation using the 338 source.

TABLE 9

Oleic acid content of canola fatty acid profile × low oleic acid F1 *B. juncea* individuals - Round 2 - project SJ-210.

| Cross | <50 | 50-55 | 55-60 | >60 |
|---|---|---|---|---|
| 02SJ-1992 | 5 | 8 | 0 | 0 |
| 02SJ-1996 | 7 | 8 | 0 | 0 |
| 02SJ-1998 | 4 | 11 | 0 | 0 |
| 02SJ-2000 | 5 | 10 | 0 | 0 |
| 02SJ-2002 | 2 | 13 | 0 | 0 |
| 02SJ-2004 | 6 | 9 | 0 | 0 |
| 02SJ-2006 | 8 | 7 | 0 | 0 |
| 02SJ-2008 | 7 | 7 | 0 | 0 |
| 02SJ-2010 | 6 | 9 | 0 | 0 |
| 02SJ-2012 | 7 | 4 | 0 | 0 |
| 02SJ-2014 | 13 | 2 | 0 | 0 |
| 02SJ-2016 | 2 | 12 | 0 | 0 |
| 02SJ-2018 | 9 | 6 | 0 | 0 |
| 02SJ-2026 | 4 | 11 | 0 | 0 |
| 02SJ-2028 | 2 | 12 | 0 | 0 |
| 02SJ-2032 | 6 | 8 | 0 | 0 |
| 02SJ-2036 | 4 | 10 | 1 | 0 |

Our first assessment of the 338 oleic acid-derived plant in the spring of 2000 was that it was a valuable source of the oleic acid trait, but did not have many of the other characteristics desirable in a canola quality *B. juncea* variety. It appeared to have extremely low oil content and high glucosinolate content, but it was acceptable as a source of canola fatty acid profile.

During the summer of 2000, an experiment was done to characterize the canola fatty acid profile stability and to determine whether any additional phenotypic changes had occurred as a result of mutation breeding. Individual seeds from the 1629 and 338 oleic acid sources were planted and evaluated for phenotypic and quality traits. Glucosinolate content was evaluated using High Performance Liquid Chromatography (HPLC) of seed samples collected from individual rows and bulked to equal weight from the different sources. Two replicates of the individual samples were collected and analyzed. The fatty acid stability was confirmed as shown above. However, there was a significant increase in glucosinolate content in these two sources compared with non-canola fatty acid profile *B. juncea* material developed in this experiment (Table 10) and as compared with the low glucosinolate *B. juncea* checks—JS0350BC and JS0351BC.

TABLE 10

Variation in glucosinolate content as determined by HPLC - glucosinolates are expressed in μmoles/g

| SOURCE | T2OH3B[1] | T2OH4P[2] | T3BUT[3] | T4PEN[4] | ALLYL[5] | INDOL[6] | TOTAL |
|---|---|---|---|---|---|---|---|
| JS0351BC | 2.98 | 0.09 | 2.81 | 0.20 | 1.38 | 6.78 | 14.24 |
| JS0351BC | 2.95 | 0.08 | 2.72 | 0.23 | 1.35 | 7.19 | 14.52 |
| JS0350BC | 2.65 | 0.03 | 1.42 | 0.15 | 2.68 | 6.09 | 13.02 |
| JS0350BC | 2.48 | 0.01 | 1.36 | 0.14 | 2.69 | 6.08 | 12.76 |
| 338 Source | 9.23 | 0.05 | 8.54 | 0.21 | 3.16 | 8.43 | 29.62 |
| 338 Source | 9.43 | 0.05 | 8.42 | 0.23 | 3.00 | 8.00 | 29.13 |
| 1629 Source | 14.60 | 0.10 | 16.79 | 0.39 | 0.24 | 8.61 | 40.73 |
| 1629 Source | 14.81 | 0.09 | 17.61 | 0.41 | 0.57 | 7.69 | 41.18 |

[1]T2OH3B = 2-hydroxy-3-butenyl
[2]T2OH4P = 2 hydroxy-4-pentenyl
[3]T3BUT = 3-butenyl
[4]T4PEN = 4-pentenyl
[5]ALLYL = Allyl glucosinolate
[6]INDOL = Indol glucosinolates Experiment 5

Variation in Glucosinolate Content

When developing a new trait, among the first things that is evaluated is the effect on other traits, which is called pleiotropy. In this case, EMS seed mutagenesis was used to develop a canola fatty acid profile in a derived population. The mutagenized lines were evaluated to assess if any other changes were produced.

The two sources of oleic acid content were very high in glucosinolate content in the summer of 2000—approximately double the glucosinolate content of two of the low glucosinolate *B. juncea* checks in the experiment. The total glucosinolate content in these lines ranged from approximately 28 to 42 μmoles/g. The 338 source was slightly lower in total glucosinolates than the 1629 source, but both would be beyond the acceptable ranges for canola variety registration in Canada. Both of these glucosinolate levels lie outside the range expressed by Potts, et al., 2001.

In the fall of 2000, some of the original 338 self-pollinated lines produced in SJ-135 were sent to a winter nursery for seed increase to produce replicated yield trials in the spring of 2001. Fifty-one lines from this seed increase were tested in the 2001 yield testing program. During the season, agronomic information was collected and in the fall, large seed samples were collected to conduct analysis to support stability of the fatty acid composition. Seed was collected, bulked and submitted to the POS Pilot Plant Corporation, 118 Veterinary Road, Saskatoon, Saskatchewan for analysis (Table 12). A duplicate sample was analyzed using HPLC and GC to determine the glucosinolate content and fatty acid composition (Tables 11 and 13).

TABLE 11

2001 Glucosinolate results - 338 source analyzed at Pioneer Hi-Bred HPLC Bulks collected at 6 locations

| SOURCE | T2OH3B | T2OH4P | T3BUT | T4PEN | ALLYL | INDOL | TOTAL |
|---|---|---|---|---|---|---|---|
| 2001 338 Source | 16.92 | 0.00 | 18.88 | 0.83 | 0.53 | 6.14 | 43.30 |

TABLE 12

2001 Glucosinolate results - 338 source analyzed at POS Pilot Plant - HPLC bulks collected at 6 locations (HP4178.xls)

| SOURCE | T2OH3B | T2OH4P | T3BUT | T4PEN | ALLYL | INDOL | TOTAL |
|---|---|---|---|---|---|---|---|
| 2001 338 whole seed | 23.1 | 1.2 | 24.2 | 0.6 | 0.6 | 4.1 | 53.8 |
| 2001 338 meal | 21.8 | 0.6 | 23.5 | 1.1 | 0.6 | 3.8 | 51.4 |

The 338 oleic source had greater than 30 μmoles of total glucosinolates in 2001 using both the Pioneer and POS Pilot Plant testing (range of 36 to 54 umol/g; see Tables 11, 12 and 13). The glucosinolate level was greater than the level acceptable for canola and approaches the levels found in traditional B. juncea mustard. Results using Scanning NIR also supported the conclusion that 338-derived lines were high in glucosinolate content.

TABLE 13

Oil content, protein content and glucosinolate content of individual 338-derived B. juncea lines (JS0737 to JS0745) - 2001 multi-location data - NIR - duplicate samples

| SOURCE | OIL % | PRO % | GLUC umol/g | C18:1 |
|---|---|---|---|---|
| JS0737 | 35.57 | 32.01 | 39.36 | 59.3 |
| JS0737 | 35.15 | 32.39 | 38.45 | 59.3 |
| JS0746 | 35.42 | 33.19 | 37.42 | 53.1 |
| JS0746 | 34.93 | 33.17 | 37.41 | 53.1 |
| JS0758 | 36.56 | 31.65 | 37.26 | 60.81 |
| JS0745 | 37.75 | 31.84 | 36.99 | 63.22 |
| JS0758 | 36.22 | 32.22 | 36.42 | 60.81 |
| JS0745 | 37.13 | 31.95 | 36.27 | 63.22 |
| 46A65 | 44.13 | 28.32 | 19.74 | 61.62 |
| 46A65 | 45.62 | 29.30 | 19.73 | 62.57 |
| JS0350 | 42.10 | 29.99 | 14.21 | 45.52 |
| JS0350 | 39.81 | 32.11 | 14.06 | 46.25 |

In an effort to develop canola quality meal, the high oleic acid selections from 2001 selected for other characteristics such as yield and oil content were crossed with other proprietary low glucosinolate sources of B. juncea. Selection for low glucosinolates and high oleic acid was done during the breeding process to develop canola quality B. juncea. During the 2002 field season, several of these canola fatty acid profile lines were evaluated. Combinations of the canola fatty acid profile with the low glucosinolate B. juncea types were identified (Table 14). There continued to be high glucosinolate lines produced from this second round of crossing, but none of them approached the high glucosinolate levels of the original 338 source. Of the selections listed in Table 14, 02SJ-4958, 02-SJ4918, 02SJ-4878, and 02SJ-4877 comprise a stable canola fatty acid profile and a canola meal profile. The total glucosinolate content ranged from approximately 8 umol/gm to 27 umol/gm indicating that a stable "canola" oil and meal profile was developed in B. juncea.

TABLE 14

Oil content, glucosinolate content and oleic acid content of second round lines selected for canola quality traits

| VARIETY | % Oil | Total Gluc μmol/gm | C18:1 |
|---|---|---|---|
| 02SJ-4891 | 38.16 | 26.67 | 58.26 |
| 02SJ-4915 | 44.07 | 23.83 | 56.14 |
| 02SJ-4872 | 43.66 | 22.12 | 55.39 |
| 02SJ-4910 | 44.67 | 21.04 | 60.86 |
| 02SJ-4946 | 42.85 | 20.62 | 60.14 |
| 02SJ-4958 | 46.89 | 9.73 | 59.25 |
| 02SJ-4918 | 47.47 | 8.95 | 59.30 |
| 02SJ-4878 | 46.47 | 8.91 | 58.63 |
| 02SJ-4918 | 46.78 | 8.71 | 59.62 |
| 02SJ-4918 | 48.03 | 8.23 | 58.12 |
| 02SJ-4877 | 44.91 | 8.22 | 58.38 |
| JS0350BC | 42.81 | 14.23 | 45.83 |

The complete fatty acid profile of 338, 1629 and 2397 was determined as shown in Table 15. New B. juncea lines having a canola fatty acid profile (as defined on page 11) and low erucic acid have been developed (Table 15). These lines produce a vegetable oil having a fatty acid composition that would be accepted as a canola-equivalent oil following crushing and extraction.

TABLE 15

Complete fatty acid profile of 338, 1629 and 2397 source
fatty acid profiles as developed by EMS seed mutagenesis

| Source | C16:0 | C18:0 | C18:1 | C18:2 | C18:3 | C20:0 | C20:1 | C22:0 | C22:1 | C24:0 | TSATS |
|---|---|---|---|---|---|---|---|---|---|---|---|
| 338 | 3.75 | 1.67 | 62.45 | 16.59 | 12.96 | 0.51 | 1.48 | 0.26 | 0.06 | 0.28 | 6.19 |
| 1629 | 4.40 | 1.65 | 61.74 | 21.49 | 7.97 | 0.67 | 1.34 | 0.38 | 0.00 | 0.37 | 7.47 |
| 2397 | 3.95 | 1.84 | 66.12 | 19.79 | 5.54 | 0.68 | 1.40 | 0.34 | 0.02 | 0.31 | 7.12 |
| B. napus | 3.54 | 1.80 | 65.77 | 19.31 | 7.16 | 0.64 | 1.29 | 0.34 | 0.00 | 0.15 | 6.47 |

These lines produced a broad range of disease resistance, oil content and yield potential. Table 16 summarizes the agronomic characteristics of these lines. Lines JS0730 through JS0749 were all derived from the 338 oleic acid source material and compared to a non-canola fatty acid B. juncea check—JS0350BC and B. napus check, 46A65. The 338-derived lines produced a range of agronomic traits such as days from planting until first flower (DYSFLW), plant height at maturity (HGT) and days from planting until physiological maturity (MAT). Many of the lines showed reduced oil content in mature seeds (OILR) and elevated protein content in mature seeds (PRO %) as compared to the B. napus and B. juncea check. Many of the lines had much higher glucosinolate content (GLC), expressed as μmole glucosinolates/gram of meal, than the B. napus or B. juncea checks and would be considered to be non-canola for glucosinolate content despite having an oleic acid (C18:1) level of greater than 55%. The 338-derived lines produced a lower yield (Yield % of 46A65) than the B. napus and B. juncea checks. This was expected as these lines were essentially not selected for basic agronomic traits. Some of the lines demonstrated a strong level of blackleg resistance which is common in many B. juncea varieties. B. juncea has been identified as having different genes for blackleg resistance than B. napus (Woods, et al., 1991). Blackleg resistance can be rated using a 1 to 9 internal scale for blackleg infection where 1 is severely infected and 9 is highly resistant. The B. napus check variety 46A65 is generally regarded as resistant to most strains of blackleg found in Canada. Check varieties are used to assess trial quality, including 46A65 as a resistant check.

TABLE 16

Agronomic performance of 338-derived breeding lines in 2001.

| VARIETY | DYSFLW | HGT | MAT | OIL % | NM % | PRO % | GLC | C18:1 | BLACKLEG RESISTANCE | YLD % 46A65 |
|---|---|---|---|---|---|---|---|---|---|---|
| JS0730 | 41.9 | 94.5 | 87.5 | 38.83 | 38.93 | 30.17 | 30.37 | 55.83 | 7.5 | 83 |
| JS0731 | 46.8 | 96.8 | 88.0 | 39.40 | 39.17 | 29.83 | 31.22 | 62.06 | 8.4 | 82 |
| JS0732 | 44.3 | 89.3 | 87.3 | 37.43 | 37.72 | 30.41 | 30.17 | 60.60 | 7.6 | 80 |
| JS0733 | 46.0 | 87.8 | 85.7 | 39.67 | 41.38 | 29.77 | 33.48 | 63.73 | 8.5 | 92 |
| JS0734 | 45.1 | 90.5 | 88.8 | 38.62 | 39.71 | 31.00 | 33.63 | 62.67 | 8.1 | 84 |
| JS0735 | 45.3 | 97.2 | 87.2 | 35.21 | 39.80 | 27.18 | 29.80 | 56.50 | 6.3 | 85 |
| JS0736 | 44.3 | 91.5 | 85.5 | 41.32 | 42.50 | 29.28 | 25.90 | 65.41 | 6.5 | 86 |
| JS0737 | 44.9 | 95.0 | 87.8 | 37.00 | 37.61 | 30.94 | 34.88 | 60.92 | 7.9 | 92 |
| JS0742 | 45.5 | 89.0 | 87.7 | 33.08 | 37.12 | 27.83 | 29.53 | 53.54 | 5.2 | 79 |
| JS0744 | 44.9 | 89.5 | 87.8 | 38.27 | 38.76 | 30.02 | 33.87 | 60.94 | 8.1 | 98 |
| JS0745 | 44.4 | 90.3 | 88.5 | 39.07 | 39.71 | 30.44 | 35.02 | 63.05 | 8.7 | 87 |
| JS0747 | 47.0 | 96.3 | 88.2 | 38.26 | 38.18 | 30.71 | 31.17 | 61.85 | 7.3 | 80 |
| JS0749 | 42.5 | 90.8 | 86.3 | 44.40 | 44.66 | 26.87 | 34.35 | 59.24 | 8.1 | 116 |
| JS0350 | 45.8 | 95.0 | 88.2 | 41.64 | 43.44 | 28.69 | 15.07 | 66.72 | 6.9 | 114 |
| 46A65 | 48.8 | 74.0 | 89.5 | 36.89 | 43.66 | 24.58 | 17.43 | 64.69 | 8.1 | |

These lines are beneficial because they will allow canola quality oil to be produced on drought-prone land that traditionally could not support a canola crop, for example the southern Canadian prairies, western Australia, and north-central US. Further, *B. juncea* has superior resiliency and productivity over existing *Brassica* species. *B. juncea* is generally high yielding, tolerant to both heat and drought, and disease resistant. Further, *B. juncea* is generally resistant to pod shattering and has a yellow seed color which may represent an improved meal quality as compared to traditionally dark-seeded *B. napus*.

In addition, new *B. juncea* lines having a canola fatty acid profile, and having high glucosinolates and low erucic acid, have also been developed. These lines would be considered mustard quality. These lines would offer the mustard industry the ability to produce a high glucosinolate meal product for the mustard industry and still produce a canola fatty acid profile oil.

The applicants' teachings include methods of producing new lines of *B. juncea* having a canola fatty acid profile. FIG. 9 is a flow chart of the methods used in the applicants' teaching.

Further Embodiments of the Invention

The applicants' teaching also includes methods of using the source material, 338, 1629 and 2397, for breeding other lines. For example, the source materials can be self-pollinated, outcrossed, backcrossed, used to produce doubled haploids, used as source materials for genetic transformation, further mutagenized, and used for other forms of breeding as is known to those skilled in the art. The methods and results of using the source material to breed other lines are also within the scope of the applicant's teaching.

For example, the source materials, 338, 1629 and 2397 can be used to produce inbred lines for hybrid seed production if they are backcrossed onto a cytoplasmic male sterility source or some other source for sterilizing the inbred line as a female. Alternatively, the line can be used directly. For example, inbred *B. juncea* canola line 338 can be crossed with another canola plant to form a first generation population of F1 plants. The population of first generation F1 plants produced by this method is also an embodiment of the applicants' teaching. This first-generation population of F1 plants will comprise an essentially complete set of the alleles of inbred canola line 338. Typically in the art an F1 hybrid is considered to have all the alleles of each parent. One of ordinary skill in the art can utilize either breeder books or molecular methods to identify a particular F1 plant produced using inbred canola line 338, and any such individual plant is also encompassed by this invention. These embodiments also cover use of these methods with transgenic or single gene conversions of inbred canola line 338.

Another embodiment of this invention is a method of using canola line 338 in breeding that involves the repeated backcrossing to inbred canola line 338 any number of times. Using backcrossing methods, or the transgenic methods described herein, the single gene conversion methods described herein, or other breeding methods known to one of ordinary skill in the art, one can develop individual plants and populations of plants that retain at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% of the genetic profile of inbred canola line 338. The percentage of the genetics retained in the progeny may be measured by either pedigree analysis or through the use of genetic techniques such as molecular markers or electrophoresis. In pedigree analysis, on average 50% of the starting germplasm would be passed to the progeny line after one cross to another line, 25% after another cross to a different line, and so on. Molecular markers could also be used to confirm and/or determine the pedigree of the progeny line.

A specific method for producing a line derived from inbred canola line 338 is as follows. One of ordinary skill in the art would cross inbred canola line 338 with another canola plant, such as an elite line. The F1 seed derived from this cross would be grown to form a homogeneous population. The F1 seed would contain 100% of the alleles from inbred canola line 338 and 100% of the alleles of the other plant. The F1 seed would be grown and allowed to self, thereby forming F2 seed. On average the F2 seed would have derived 50% of its alleles from variety 338 and 50% from the other canola plant, but various individual plants from the population would have a much greater percentage of their alleles derived from 338 (Wang, et al., (2000) *Crop Sci.* 40:659-665 and Bernardo, et al., (2001) *Theor. Appl. Genet.* 102:986-992). As used in this context, the term population refers to a statistically representative sample. The F2 seed would be grown and selection of plants would be made based on visual observation and/or measurement of traits. The traits used for selection may be the canola line 338 trait of high oleic oil. The 338-derived progeny that exhibits the desired 338-derived trait would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as the desirable 338-derived trait listed above. The process of growing and selection would be repeated any number of times until an inbred 338-derived canola plant is obtained. The inbred 338-derived canola plant would contain desirable traits derived from canola line 338, some of which may not have been expressed by the other canola plant to which canola line 338 was crossed and some of which may have been expressed by both canola lines but now would be at a level equal to or greater than the level expressed in 338. The inbred 338-derived canola plants would have, on average, 50% of their genes derived from 338, but various individual plants from the population would have a much greater percentage of their alleles derived from 338. The breeding process, of crossing, self-pollination, and selection may be repeated to produce another population of 338-derived canola plants with, on average, 25% of their genes derived from canola line 338, but various individual plants from the population would have a much greater percentage of their alleles derived from 338. Another embodiment of the invention is an inbred 338-derived canola plant that has received the desirable 338-derived trait of high oleic acid.

The previous example can be modified in numerous ways, for instance selection may or may not occur at every self-pollinated generation, selection may occur before or after the actual self-pollination process occurs, or individual selections may be made by harvesting individual pods, plants, rows or plots at any point during the breeding process described. In addition, doubled-haploid breeding methods may be used at any step in the process. The population of plants produced at each and any generation of self-pollination is also an embodiment of the invention, and each such population would consist of plants containing approximately 50% of its genes from canola line 338, 25% of its genes from canola line 338 in the second cycle of crossing, selfing, and selection, 12.5% of its genes from canola line 338 in the third cycle of crossing, selfing, and selection, and so on.

Another embodiment of this invention is the method of obtaining a homozygous 338-derived canola plant by crossing canola line 338 with another canola plant and applying doubled-haploid methods to the F1 seed or F1 plant or to any generation of canola line 338 obtained by the selfing of this cross.

Still further, this invention also is directed to methods for producing 338-derived canola plants by crossing canola line 338 with a canola plant and growing the progeny seed, and repeating the crossing with the growing steps with the 338-derived canola plant from 1 to 2 times, 1 to 3 times, 1 to 4 times, or 1 to 5 times and selfing any number of times after the first, second, third, fourth, or fifth cross. Thus, any and all methods using canola line 338 in breeding are part of this invention, including selfing, pedigree breeding, backcrosses, hybrid production and crosses to populations. All plants and populations of plants produced using canola line 338 as a parent are within the scope of this invention. Unique molecular marker profiles and/or breeding records can be used by those of ordinary skill in the art to identify the progeny lines or populations of progeny derived from canola line 338.

All plants produced using canola line 338 as a parent are within the scope of this invention, including those developed from varieties derived from inbred canola line 338.

A further embodiment of the invention is a single-gene conversion of 338. A single-gene conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to, fertility modification, fatty acid profile modification, other nutritional enhancements, industrial enhancements, disease resistance, insect resistance, herbicide resistance and yield enhancements. The trait of interest is transferred from the donor parent to the recurrent parent, in this case, the canola plant disclosed herein. Single gene traits may result from the transfer of either a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest. Along with selection for the trait of interest, progeny are selected for the phenotype of the recurrent parent. It should be understood that occasionally additional polynucleotide sequences or genes are transferred along with the single gene conversion trait of interest. A progeny containing at least 90%, 95%, 96%, 97%, 98%, 99% or 99.5% of the genes from the recurrent parent, the canola plant disclosed herein, plus containing the single-gene-conversion trait, is considered to be a single-gene conversion of 338.

It should be understood that the canola line of the invention can, through routine manipulation of cytoplasmic genes, nuclear genes, or other factors, be produced in a male-sterile form as described in the references discussed earlier. Such embodiments are also within the scope of the present claims. Canola line 338 can be manipulated to be male sterile by any of a number of methods known in the art, including by the use of mechanical methods, chemical methods, self-incompatibility (SI), cytoplasmic male sterility (CMS, either ogura or another system) or nuclear male sterility (NMS). The term "manipulated to be male sterile" refers to the use of any available techniques to produce a male sterile version of canola line 338. The male sterility may be either partial or complete male sterility. This invention is also directed to F1 hybrid seed and plants produced by the use of canola line 338.

This invention is also directed to the use of 338 in plant cell culture and tissue culture. The applicants' teachings include plants and plant parts from the disclosed lines, as well as other plants produced by the methods disclosed. As used herein, the term plant includes plant protoplasts, plant cell tissue cultures from which canola plants can be regenerated, plant calli, plant clumps, and plant cells that are intact in plants or parts of plants, such as embryos, pollen, ovules, seeds, flowers, ears, silique, leaves, stems, roots, root tips, anthers, cotyledons and the like, all of which are within the scope of the applicants' teaching. Tissue culture as well as microspore culture for regeneration of canola plants can be accomplished successfully. Chuong, et al., (1985) "A Simple Culture Method for *Brassica* hypocotyl Protoplasts", *Plant Cell Reports* 4:4-6; Barsby, et al., (Spring 1996) "A Rapid and Efficient Alternative Procedure for the Regeneration of Plants from Hypocotyl Protoplasts of *Brassica napus*", *Plant Cell Reports*; Kartha, et al., (1974) "In vitro Plant Formation from Stem Explants of Rape", *Physiol. Plant,* 31:217-220; Narasimhulu, et al., (Spring 1988) "Species Specific Shoot Regeneration Response of Cotyledonary Explants of *Brassicas*", *Plant Cell Reports*; Swanson, (1990) "Microspore Culture in *Brassica*", *Methods in Molecular Biology,* 6(17):159. "Cell Culture techniques and Canola improvement" *J. Am. Oil Chem. Soc.* 66(4):455-56, (1989). Thus, it is clear from the literature that the state of the art is such that these methods of obtaining plants are, and were, "conventional" in the sense that they are routinely used and have a very high rate of success.

The utility of canola line 338 also extends to crosses with other species. Commonly, suitable species will be of the family Brassicacea.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome of the species using transformation are referred to herein collectively as "transgenes". The process of "transforming" is the insertion of DNA into the genome. Over the last fifteen to twenty years several methods for producing transgenic plants have been developed, and the present invention, in particular embodiments, also relates to transformed versions of the claimed canola line 338.

Numerous methods for plant transformation have been developed, including biological and physical, plant transformation protocols. See, for example, Miki, et al., "Procedures for Introducing Foreign DNA into Plants" in Methods in *Plant Molecular Biology and Biotechnology*, Glick, B. R. and Genetic Transformation for the improvement of Canola World Conf, Biotechnol Fats and Oils Ind. 43-46, 1988. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular canola plant using transformation techniques could be moved into another line using traditional breeding techniques that are well known in the plant breeding arts. For example, a backcrossing approach could be used to move a transgene from a transformed canola plant to an elite inbred line and the resulting progeny would comprise a transgene. Also, if an inbred line was used for the transformation then the transgenic plants could be crossed to a different line in order to produce a transgenic hybrid canola plant. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. See, U.S. Pat. No. 6,222,101 which is herein incorporated by reference.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, (1981) *Anal. Biochem.* 114:92-6.

A genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule coding for the foreign protein. For exemplary methodologies in this regard, see Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, plants can be genetically engineered to express various phenotypes of agronomic interest. Exemplary transgenes implicated in this regard include, but are not limited to, those categorized below.

1. Genes That Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) Science 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*).

(B) A gene conferring resistance to fungal pathogens, such as oxalate oxidase or oxalate decarboxylase (Zhou, et al., (1998) *Pl. Physiol.* 117(1):33-41).

(C) A *Bacillus thuringiensis* protein, a derivative thereof or a synthetic polypeptide modeled thereon. See, for example, Geiser. et al., (1986) *Gene* 48:109, who disclose the cloning and nucleotide sequence of a Bt δ-endotoxin gene. Moreover, DNA molecules encoding δ-endotoxin genes can be purchased from American Type Culture Collection (Manassas, Va.), for example, under ATCC Accession Numbers 40098, 67136, 31995 and 31998.

(D) A lectin. See, for example, the disclosure by Van Damme, et al., (1994) *Plant Molec. Biol.* 24:25, who disclose the nucleotide sequences of several *Clivia miniata* mannose-binding lectin genes.

(E) A vitamin-binding protein such as avidin. See, PCT Application Number US93/06487, the contents of which are hereby incorporated by reference. The application teaches the use of avidin and avidin homologues as larvicides against insect pests.

(F) An enzyme inhibitor, for example, a protease or proteinase inhibitor or an amylase inhibitor. See, for example, Abe, et al., (1987) *J. Biol. Chem.* 262:16793 (nucleotide sequence of rice cysteine proteinase inhibitor), Huub, et al., (1993) *Plant Molec. Biol.* 21:985 (nucleotide sequence of cDNA encoding tobacco proteinase inhibitor I), Sumitani, et al., (1993) *Biosci. Biotech. Biochem.* 57:1243 (nucleotide sequence of *Streptomyces nitrosporeus* α-amylase inhibitor) and U.S. Pat. No. 5,494,813 (Hepher and Atkinson, issued Feb. 27, 1996).

(G) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344:458, of baculovirus expression of cloned juvenile hormone esterase, an inactivator of juvenile hormone.

(H) An insect-specific peptide or neuropeptide which, upon expression, disrupts the physiology of the affected pest. For example, see the disclosures of Regan, (1994) *J. Biol. Chem.* 269:9 (expression cloning yields DNA coding for insect diuretic hormone receptor), and Pratt, et al., (1989) *Biochem. Biophys. Res. Comm.* 163:1243 (an allostatin is identified in *Diploptera puntata*). See also, U.S. Pat. No. 5,266,317 to Tomalski, et al., who disclose genes encoding insect-specific, paralytic neurotoxins.

(I) An insect-specific venom produced in nature by a snake, a wasp, etc. For example, see, Pang, et al., (1992) *Gene* 116:165, for disclosure of heterologous expression in plants of a gene coding for a scorpion insectotoxic peptide.

(J) An enzyme responsible for an hyperaccumulation of a monterpene, a sesquiterpene, a steroid, hydroxamic acid, a phenylpropanoid derivative or another non-protein molecule with insecticidal activity.

(K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 93/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene.

(L) A molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(M) A hydrophobic moment peptide. See, PCT Application Number WO95/16776 (disclosure of peptide derivatives of Tachyplesin which inhibit fungal plant pathogens) and PCT Application Number WO95/18855 (teaches synthetic antimicrobial peptides that confer disease resistance), the respective contents of which are hereby incorporated by reference.

(N) A membrane permease, a channel former or a channel blocker. For example, see, Jaynes, et al., (1993) *Plant Sci.* 89:43, of heterologous expression of a cecropin-β lytic peptide analog to render transgenic tobacco plants resistant to *Pseudomonas solanacearum*.

(O) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(P) An insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(Q) A virus-specific antibody. See, for example, Tavladoraki, et al., (1993) *Nature* 366:469, who show that transgenic plants expressing recombinant antibody genes are protected from virus attack.

(R) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See, Lamb et al., (1992) *Bio/Technology* 10:1436. The cloning and characterization of a gene which encodes a bean endopolygalacturonase-inhibiting protein is described by Toubart, et al., (1992) *Plant J.* 2:367.

(S) A developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(T) Genes involved in the Systemic Acquired Resistance (SAR) Response and/or the pathogenesis related genes. Briggs, (1995) *Current Biology* 5(2).

(U) Antifungal genes (Cornelissen and Melchers, Pl. Physiol. (1993) 101:709-712, and Parijs, et al. (1991), *Planta* 183:258-264 and Bushnell, et al., (1998) *Can. J. of Plant Path.* 20(2):137-149.

2. Genes That Confer Resistance to a Herbicide, for Example:

(A) A herbicide that inhibits the growing point or meristem, such as an imidazalinone or a sulfonylurea. Exemplary genes in this category code for mutant ALS and AHAS enzyme as described, for example, by Lee, et al., (1988) *EMBO J.* 7:1241, and Miki, et al., (1990) *Theor. Appl. Genet.* 80:449, respectively.

(B) Glyphosate (resistance imparted by mutant 5-enolpyruvl-3-phosphikimate synthase (EPSP) and aroA genes) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. See also U.S. Pat. No. 7,405,074, and related applications, which disclose compositions and means for providing glyphosate resistance. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in European Application Number 0 242 246 to Leemans, et al., De Greef, et al., *Bio/Technology* 7:61 (1989), describe the production of transgenic plants that express chimeric bar genes coding for phosphinothricin acetyl transferase activity. Exemplary of genes conferring resistance to phenoxy propionic acids and cyclohexones, such as sethoxydim and haloxyfop, are the Acc1-S1, Acc1-S2 and Acc1-S3 genes described by Marshall, et al., (1992) *Theor. Appl. Genet.* 83:435.

(C) A herbicide that inhibits photosynthesis, such as a triazine (psbA and gs+ genes) and a benzonitrile (nitrilase gene). Przibilla, et al., (1991) *Plant Cell* 3:169, describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173.

3. Genes that Confer or Contribute to a Value-Added Trait, Such as:

(A) Modified fatty acid metabolism, for example, by transforming a plant with an antisense gene of stearoyl-ACP desaturase to increase stearic acid content of the plant. See, Knultzon, et al., (1992) *Proc. Nat'l. Acad. Sci. USA* 89:2624.

(B) Decreased phytate content
  (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.
  (2) A gene could be introduced that reduces phytate content. In maize, this, for example, could be accomplished, by cloning and then reintroducing DNA associated with the single allele which is responsible for maize mutants characterized by low levels of phytic acid. See, Raboy, et al., (1990) *Maydica* 35:383.

(C) Modified carbohydrate composition effected, for example, by transforming plants with a gene coding for an enzyme that alters the branching pattern of starch. See, Shiroza, et al., *J. Bacteriol.* 170:810 (1988) (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* α-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley α-amylase gene), and Fisher, et al., (1993) *Plant Physiol.* 102: 1045 (maize endosperm starch branching enzyme II).

(D) Reduced green seed, by down regulation of the CAB gene in Canola seed (Abstract #1566, Am. Soc. Pl. Physiol. Meeting 1997, Morisette et al.

(E) Elevated oleic acid via FAD-2 gene modification and/or decreased linolenic acid via FAD-3 gene modification (see, U.S. Pat. Nos. 6,063,947; 6,323,392; and WO 93/11245).

4. Genes that Control Pollination or Hybrid Seed Production:
See, for example, the disclosures of WO92/01799 and WO98/35052.

Although the various breeding techniques are discussed herein with reference to high oleic line 338, it is to be understood that the breeding techniques could be used in conjunction with 1629 and 2397.

INDUSTRIAL APPLICABILITY

The seed of the 338, 1629 and 2397 lines, or seed of progeny of these lines, the plant produced from such seed or progeny thereof, the hybrid plants produced from the crossing of the lines or progeny lines thereof, the resulting hybrid seed, and various parts of the plants can be utilized in the production of an edible vegetable oil or other food products in accordance with known techniques. The remaining solid meal component derived from seeds of the lines, progeny lines or hybrids produced from the lines or progeny lines can be used as a nutritious livestock feed.

Deposits

Deposits of the seed of the new 338 *Brassica juncea* canola line are and have been maintained by Pioneer Hi-Bred International, Inc., 800 Capital Square, 400 Locust Street, Des Moines, Iowa 50309-2340, since prior to the filing date of this application. Access to these deposits will be available during the pendency of the application only to the Commissioner of Patents and Trademarks and persons determined by the Commissioner, under 37 CFR §1.14 and 35 U.S.C. 122, to be entitled thereto upon request. Upon the maturation of this application into a patent, and in accordance with the scope of the issued claims, Applicant(s) will make available to the public without restriction a deposit of at least 2,500 seeds of the 338 line deposited at the American Type Culture Collection (ATCC), Manassas, Va. 20110-2209. The seeds deposited with the ATCC will be taken from the same deposits maintained at Pioneer Hi-Bred International, Inc. and described above. Additionally, Applicant(s) will comply with all of the requirements of 37 C.F.R. §§1.801-1.809, including providing an indication of the viability of the sample when the deposit is made. This deposit of the 338 line will be maintained in the ATCC, which is a public depository recognized by the Budapest Treaty, for a period of 30 years, or 5 years after the most recent request, or for the enforceable life of the patent, whichever is longer, and will be replaced if it ever becomes nonviable during that period. More specifically, seeds of 338 were deposited under the terms of the Budapest Treaty at the ATCC where they have been assigned ATCC Accession Number PTA-8533. Except as provided under 37 C.F.R. §1.808, Applicant(s) will impose no restrictions on the availability of the deposited material from the ATCC; however, Applicant(s) has/have no authority to waive any restrictions imposed by law on the transfer of biological material or its transportation in commerce. Applicant(s) does/do not waive any infringement of its rights granted under any patents or breeder's rights granted in any country including rights in the United States under this patent and/or under the Plant Variety Protection Act (7 USC 2321, et seq.).

The foregoing invention has been described in detail by way of illustration and example for purposes of exemplification. However, it will be apparent that changes and modifications such as single gene modifications and mutations, somaclonal variants, variant individuals selected from populations of the plants of the instant line, and the like, are considered to be within the scope of the present invention. All references disclosed herein whether to journal, patents, published applications and the like are hereby incorporated in their entirety by reference.

What is claimed is:

1. *Brassica juncea* line 338 and seed, representative seed of said line having been deposited under ATCC Accession Number PTA-8533.

2. A *Brassica juncea* plant, or parts thereof, produced by growing seed of *Brassica juncea* line 338, representative seed of said line having been deposited under ATCC Accession Number PTA-8533.

3. A method of breeding a 338-derived plant comprising:
   (i) obtaining the *Brassica juncea* plant, or plant parts, of claim 2;
   (ii) utilizing breeding methods to produce a 338-derived plant.

4. The method of claim 3 wherein the breeding methods are selected from the group consisting of cross pollination, self pollination, selection, tissue culture, doubled haploid production and genetic transformation.

5. A method for producing a 338-derived *Brassica juncea* plant, or parts thereof comprising:
   (a) crossing the *Brassica juncea* plant, or parts thereof, of claim 2, with a second plant to produce a first generation progeny seed;
   (b) growing said first generation progeny seed to produce an F1 generation plant;
   (c) optionally, repeating the steps of crossing and growing to obtain successive filial generations of said seed to obtain a 338-derived *Brassica juncea* seed, plant, or parts thereof.

6. The 338-derived *Brassica juncea* plant, or parts thereof, produced by the method of claim 3, wherein said plant is an $F_1$ progeny plant.

7. A method of producing oil and/or meal from the seed of claim 1, comprising:
   (i) growing the *Brassica juncea* plant of claim 2 under *Brassica* plant growing conditions;
   (ii) harvesting the seed; and
   (iii) extracting oil and/or meal.

8. A method of producing oil from *Brassica juncea* seed of claim 1 comprising:
   (i) crushing seeds of *Brassica juncea* line 338, representative seed of said line having been deposited under ATCC Accession No. PTA-8533; and
   (ii) extracting oil from said seeds.

* * * * *